United States Patent
Nett et al.

(10) Patent No.: US 9,001,960 B2
(45) Date of Patent: Apr. 7, 2015

(54) METHOD AND APPARATUS FOR REDUCING NOISE-RELATED IMAGING ARTIFACTS

(75) Inventors: Brian Edward Nett, Madison, WI (US);
Bruno De Man, Clifton Park, NY (US);
Jiang Hsieh, Brookfield, WI (US); Jed Douglas Pack, Glenville, NY (US);
Zhou Yu, Waukesha, WI (US);
Guangzhi Cao, Lafayette, IN (US)

(73) Assignee: General Electric Company, Schenectady, NY (US)

( * ) Notice: Subject to any disclaimer, the term of this patent is extended or adjusted under 35 U.S.C. 154(b) by 669 days.

(21) Appl. No.: 13/343,069

(22) Filed: Jan. 4, 2012

(65) Prior Publication Data

US 2013/0170609 A1      Jul. 4, 2013

(51) Int. Cl.
| A61B 6/03 | (2006.01) |
| A61B 6/00 | (2006.01) |
| G06T 5/00 | (2006.01) |
| G06T 5/50 | (2006.01) |
| G06T 11/00 | (2006.01) |

(52) U.S. Cl.
CPC . *G06T 5/001* (2013.01); *G06T 5/50* (2013.01); *G06T 11/008* (2013.01); *G06T 2207/10072* (2013.01); *G06T 2207/20182* (2013.01); *A61B 6/507* (2013.01); *G06T 11/006* (2013.01); *G06T 2211/412* (2013.01)

(58) Field of Classification Search
USPC .......... 378/4, 7, 46, 69, 86, 87, 210; 382/128, 382/130, 131, 132, 325
See application file for complete search history.

(56) References Cited

U.S. PATENT DOCUMENTS

| 6,845,143 | B2 * | 1/2005 | Gringauz et al. | 378/8 |
| 7,245,755 | B1 * | 7/2007 | Pan et al. | 382/131 |
| 7,283,859 | B2 * | 10/2007 | Madore | 600/410 |
| 7,792,347 | B2 * | 9/2010 | Manzke et al. | 382/131 |
| 8,055,050 | B2 * | 11/2011 | Roessl et al. | 382/131 |
| 8,401,276 | B1 * | 3/2013 | Choe et al. | 382/154 |
| 8,483,351 | B2 * | 7/2013 | Wang et al. | 378/4 |
| 2002/0156364 | A1 * | 10/2002 | Madore | 600/410 |
| 2004/0146136 | A1 * | 7/2004 | Gringauz et al. | 378/4 |
| 2006/0198291 | A1 * | 9/2006 | Teguri et al. | 369/277 |
| 2007/0248253 | A1 * | 10/2007 | Manzke et al. | 382/131 |
| 2010/0121183 | A1 * | 5/2010 | Taguchi et al. | 600/427 |
| 2010/0158144 | A1 | 6/2010 | Youm | |
| 2010/0208962 | A1 * | 8/2010 | Roessl et al. | 382/131 |
| 2011/0142313 | A1 | 6/2011 | Pack | |
| 2012/0039434 | A1 * | 2/2012 | Wang et al. | 378/11 |
| 2012/0155728 | A1 * | 6/2012 | DeMan et al. | 382/131 |
| 2012/0162002 | A1 * | 6/2012 | Semenov | 342/22 |

(Continued)

OTHER PUBLICATIONS

Autoadaptive phase-correlated (AAPC) reconstruction for 4D CBCT; Frank Bergner, Institute of Medical Physics, University of Erlangen-Nurnberg., Dec. 2009.

*Primary Examiner* — Bernard E Souw
(74) *Attorney, Agent, or Firm* — Dean Small; The Small Patent Law Group, LLC.

(57) ABSTRACT

A method for reconstructing an image of an object includes acquiring a set of measured projection data, reconstructing the measured projection data using a first algorithm to generate a first reconstructed image dataset, reconstructing the measured projection data using a second algorithm to generate a second reconstructed image dataset, the second algorithm being utilized to improve the temporal resolution of the second reconstructed image dataset, and generating a final image dataset using both the first and second image datasets.

21 Claims, 5 Drawing Sheets

(56) References Cited

U.S. PATENT DOCUMENTS

| | | | |
|---|---|---|---|
| 2013/0077843 A1* | 3/2013 | Bruder et al. | 382/131 |
| 2013/0315453 A1* | 11/2013 | Cao et al. | 382/128 |
| 2013/0321590 A1* | 12/2013 | Kirk | 348/48 |
| 2013/0338484 A1* | 12/2013 | Huang et al. | 600/411 |

\* cited by examiner

METHOD AND APPARATUS FOR REDUCING NOISE-RELATED IMAGING ARTIFACTS

BACKGROUND OF THE INVENTION

This subject matter disclosed herein relates generally to imaging systems, and more particularly, to a method and apparatus for generating images having reduced noise-related imaging artifacts.

Non-invasive imaging broadly encompasses techniques for generating images of the internal structures or regions of a person or object that are otherwise inaccessible for visual inspection. One such imaging technique is known as x-ray computed tomography (CT). CT imaging systems measure the attenuation of x-ray beams that pass through the object from numerous angles (often referred to as projection data). Based upon these measurements, a computer is able to process and reconstruct images of the portions of the object responsible for the radiation attenuation. CT imaging techniques, however, may present certain challenges when imaging dynamic internal organs, such as the heart. For example, in cardiac imaging, the motion of the heart causes inconsistencies in the projection data which, after reconstruction, may result in various artifacts such as blurring, streaking, or discontinuities. In particular, artifacts may occur during cardiac imaging when projections that are not acquired at the same point in the heart cycle, e.g., the same phase, are used to reconstruct the image.

For example, in CT reconstruction, the image function to be reconstructed is generally assumed to be stationary during the acquisition. However, the image function is a function of time as well. Therefore, motion-related artifacts may occur in the reconstructed images. In general, to reduce motion related artifacts, the image data is acquired as quickly as possible to minimize the time over which the projections which contribute to the image are acquired. However, reducing the amount of time utilized to acquire the image data results in fewer projections being acquired and thus few photons contributing to the image reconstruction. Accordingly, information from fewer total photons is available to reconstruct the final image. As a result, the final image may have increased noise because fewer projections are utilized to reconstruct the final image.

BRIEF DESCRIPTION OF THE INVENTION

In one embodiment, a method for reconstructing an image of an object is provided. The method includes acquiring a set of measured projection data, reconstructing the measured projection data using a first algorithm to generate a first reconstructed image dataset, reconstructing the measured projection data using a second algorithm to generate a second reconstructed image dataset, the second algorithm being utilized to improve the temporal resolution of the second reconstructed image dataset, and generating a final image dataset using both the first and second image datasets.

In another embodiment, an imaging system is provided. The imaging system includes an imaging scanner and a processor coupled to the imaging scanner. The processor is configured to acquire a set of measured projection data, reconstruct the measured projection data using a first algorithm to generate a first reconstructed image dataset, reconstruct the measured projection data using a second algorithm to generate a second reconstructed image dataset, the second algorithm being utilized to improve the temporal resolution of the second reconstructed image dataset, and generate a final image dataset using both the first and second image datasets.

In a further embodiment, a non-transitory computer readable medium is provided. The non-transitory computer readable medium is configured to instruct a computer to acquire a set of measured projection data, reconstruct the measured projection data using a first algorithm to generate a first reconstructed image dataset, reconstruct the measured projection data using a second algorithm to generate a second reconstructed image dataset, the second algorithm being utilized to improve the temporal resolution of the second reconstructed image dataset, and generate a final image dataset using both the first and second image datasets.

DETAILED DESCRIPTION OF THE INVENTION

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

In various embodiments, a method and/or apparatus is provided that decomposes an image object f(x, y, z, C) into multiple regions based on temporal behavior. In some regions in the image there may be no temporal dependence, e.g. the spine, while in other regions there may be significant temporal dependence, e.g. the coronary arteries. Once the object has been decomposed based on the temporal characteristics, the regions with no temporal dependence may be reconstructed using more projection data and hence the quantum noise will be reduced in these regions. The various embodiments described herein may be applied to data collected from any source trajectory. In some embodiments, the data is collected using either an axial circular trajectory or a helical trajectory which may both be utilized with a computed tomography (CT) imaging system. At least one technical effect of various embodiments is to reduce noise-related imaging artifacts.

Figure 1:
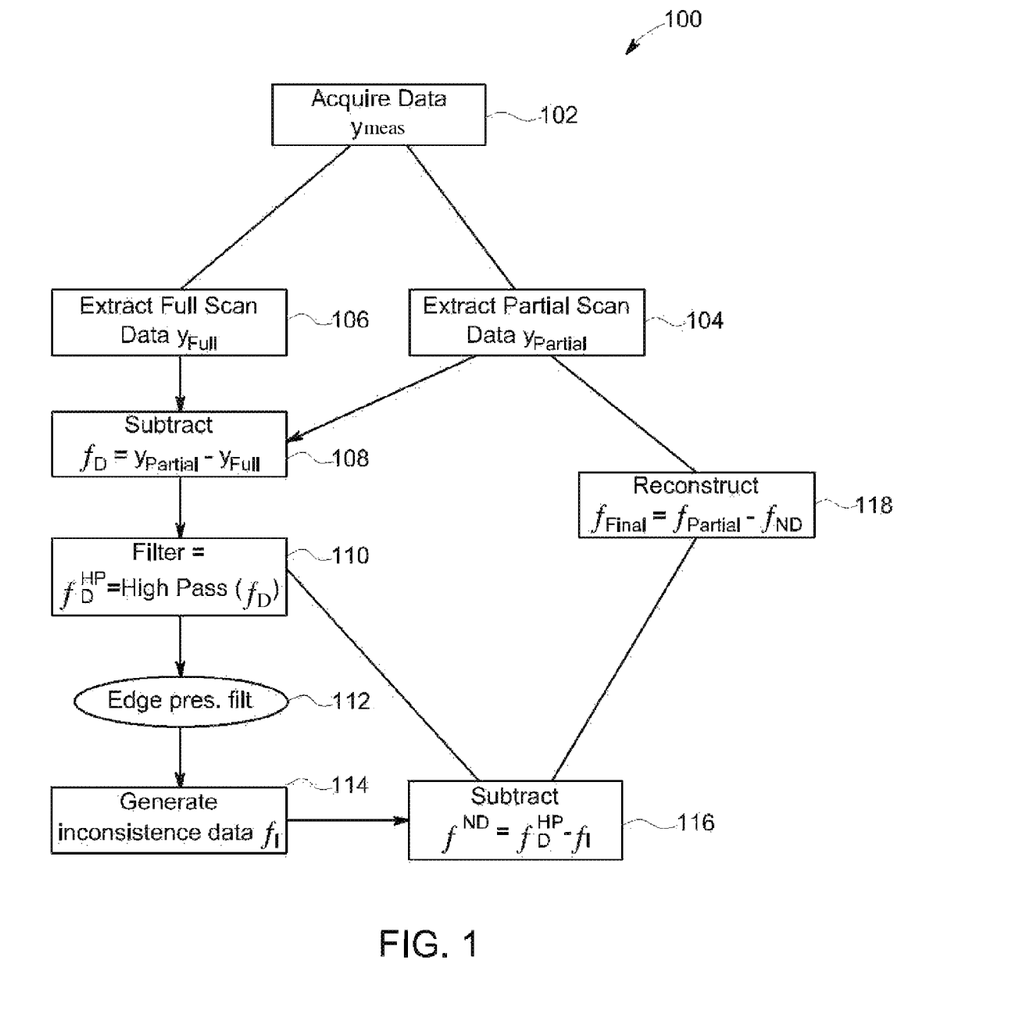
FIG. 1 is a flowchart of a method for reconstructing an image of an object in accordance with various embodiments.

FIG. 1 is a flowchart of a method 100 for reconstructing an image of an object in accordance with various embodiments.

Figure 2:
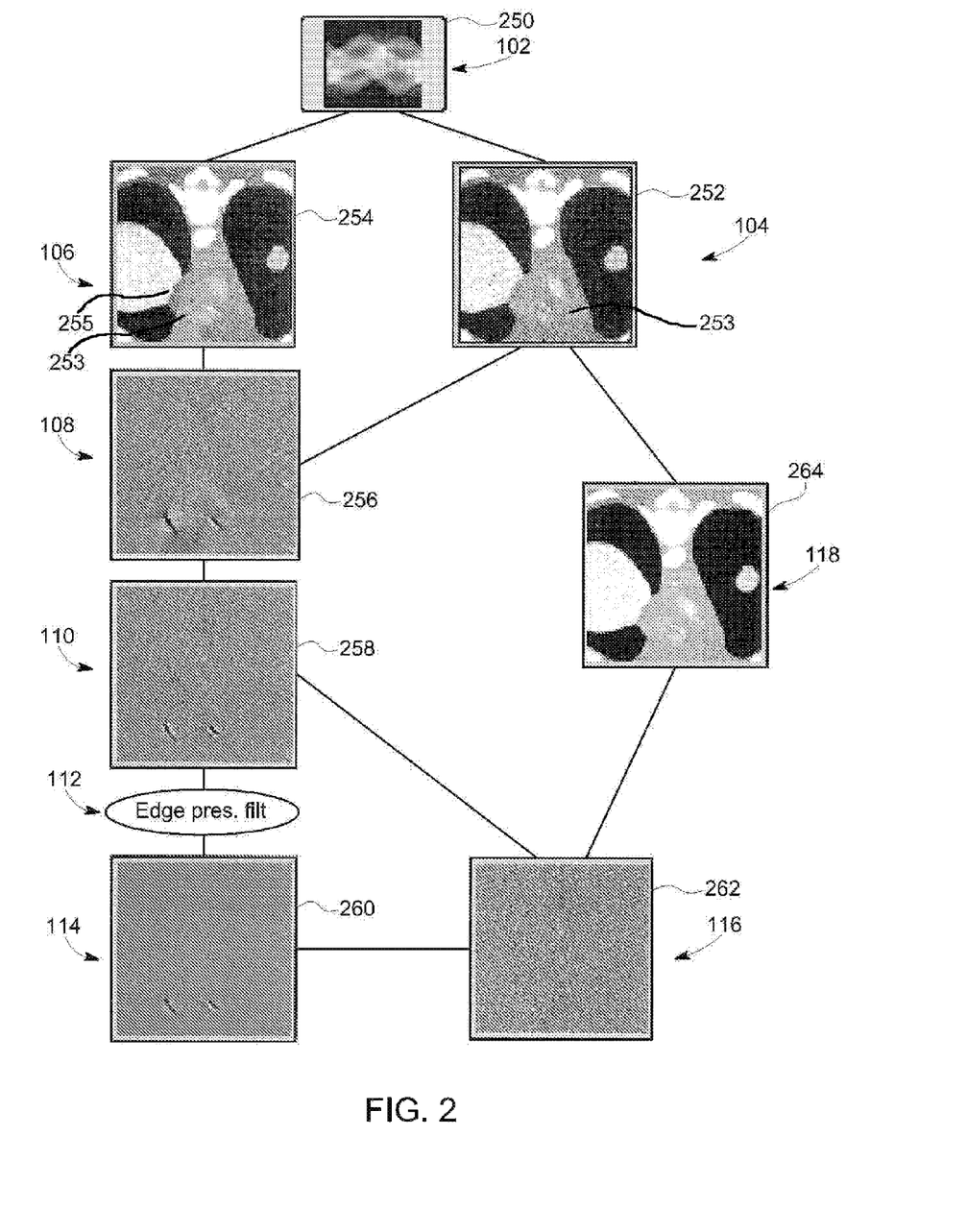
FIG. 2 is a pictorial representation of the method illustrated in FIG. 1.
Figure 6:
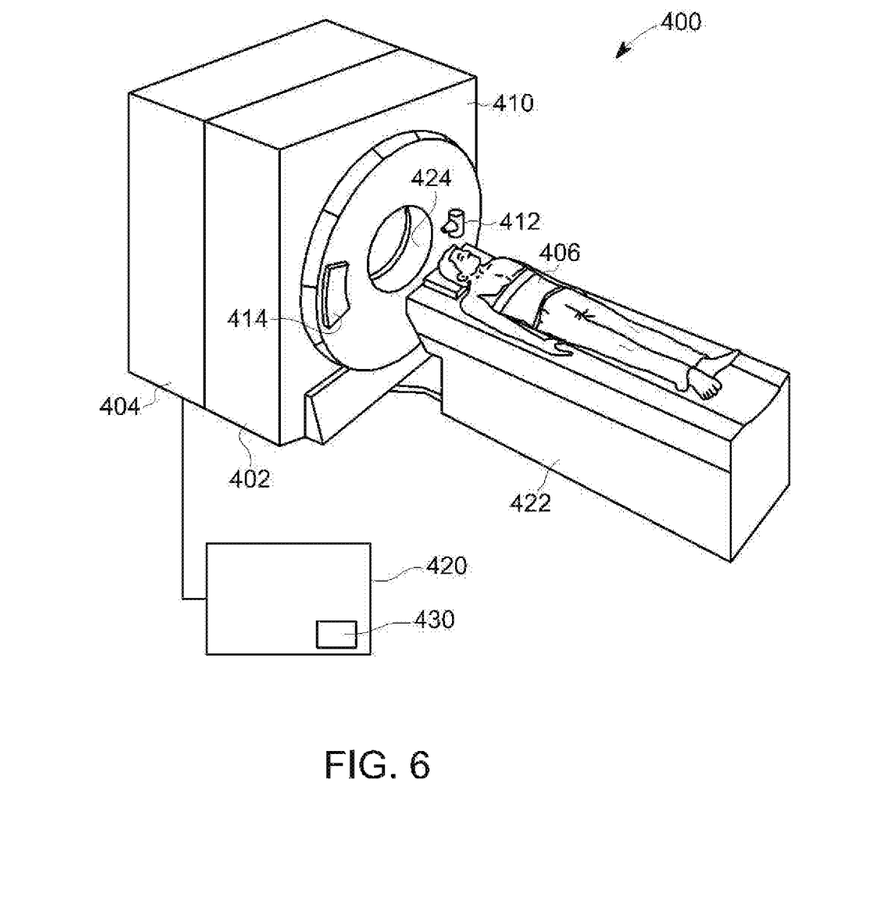
FIG. 6 is a pictorial view of a multi-modality imaging system formed in accordance with various embodiments.

In one embodiment, the method 100 is used to reconstruct an image of the heart of a subject, such as a subject 406 shown in FIG. 6, having reduced noise-related imaging artifacts. FIG. 2 is a pictorial representation of the method 100 shown in FIG. 1. The method 100 may be embodied as an algorithm that is operable to perform the methods described herein. The algorithm may be embodied as a set of instructions that are stored on a computer and implemented using, for example, a module 430, shown in FIG. 6 that is configured to implement various noise-related artifact reduction methods described herein.

Referring to FIG. 1, at 102 a subject is scanned to generate a set of projection data. In the illustrated embodiment, the subject is scanned using a full scan technique to generate the set of projection data ($y_{meas}$), or projections. The subject 406 may be scanned, using for example, the CT imaging system shown in FIGS. 6 and 7 which are discussed in more detail below. Optionally, the set of projection data $y_{meas}$ may be acquired using other imaging systems described herein. In various embodiments, the set of projection data $y_{meas}$ is acquired using a full scan of the subject to facilitate minimizing exposure of the subject to radiation administered during the full scan.

In various embodiments described herein, two image volumes may be reconstructed with different temporal resolution. These volumes will be combined such that in regions free of motion more data will be used than in regions containing motion. One embodiment of this concept is to adaptively blend a full scan and a short scan image volume. Thus, we will now introduce the terminology for full and short scan acquisitions. However, this technique is not limited to these two scan ranges. As used herein, a term full scan or full set of projection data represents a partial scan plus some additional padding which is discussed in more detail below. For example, the partial scan may be embodied as a short scan (a.k.a. a half-scan), that is a scan conducted over an angular range of 180 degrees plus the fan angle of an x-ray source. In the exemplary embodiment, the fan angle may be, for example, 60 degrees, such that the total range scanned, for a short scan, is approximately 240 degrees. However, it should be realized that different systems may have different fan angles, and therefore the scan angle of 240 degrees is exemplary only. More generally, the short scan may be acquired for an axial circular trajectory or a helical trajectory of $(\pi+\phi_{full})$ where $\phi_{full}$ is the full fan angle of the system. The full fan angle $\phi_{full}$ represents the fan angle on both sides of the x-ray source. Accordingly, in various embodiments, the fan angle on each side of the x-ray source is 30 degrees, and therefore, the full fan angle $\phi_{full}$ is 60 degrees. The partial scan may also be embodied as a super-short scan that is utilized to acquire data of only a specific region of interest. In this case a scan range of less than 180 degrees may be used as the partial scan. In various other embodiments, such as multi-beat cardiac acquisitions, the partial scan may also be embodied to acquire data beyond a standard short scan as long as it is a subset of the total data acquired.

As discussed above, the set of projection data $y_{meas}$ includes projection data acquired during the partial scan and some additional padding. The term padding, as used herein, represents additional projection data that is acquired in addition to the short scan projection data. For example, cardiac CT acquisitions may be performed using either retrospective or prospective gating. In the case of a standard retrospective helical acquisition, the projection data is acquired from all phases throughout the cardiac cycle. During the acquisition the x-ray tube current may be modulated such that the current is high during the portion of the cardiac cycle when the heart is generally most stationary. In a prospective acquisition, the projection data is specifically acquired during only the desired portion of the cardiac cycle. However, a strict prospective acquisition generally does not enable any flexibility in shifting the reconstructed phase. Therefore, to compromise between flexibility in cardiac phase reconstruction and minimal scan dose, additional projection data or padding, may be acquired. Thus, in various embodiments, the full scan includes the short scan $((\pi+\phi_{full})+P)$, wherein P is the padding.

The padding (P) may be any angular range that is greater than zero. For example, assuming that P=120 degrees for each side of the scan, then the angular range of the full scan, which includes the short scan of 240 degrees, is 360 degrees, or one full rotation of a CT gantry 410 (shown in FIG. 6). It should be realized that the padding P may have any angular range that is greater than zero degrees and that P=120 degrees is exemplary only. For example, P may be set between 0 and 120 degrees such that less than the full angular range (assumed to be 360 degrees in this example) is utilized to generate the projection data $y_{meas}$. Optionally, P may be greater than 120 degrees such that more than one gantry revolution is utilized to acquire the projection data $y_{meas}$. In various embodiments, the value for P may be manually selected by the user prior to acquiring the projection data $y_{meas}$ or may be derived and adjustable.

Figure 3:
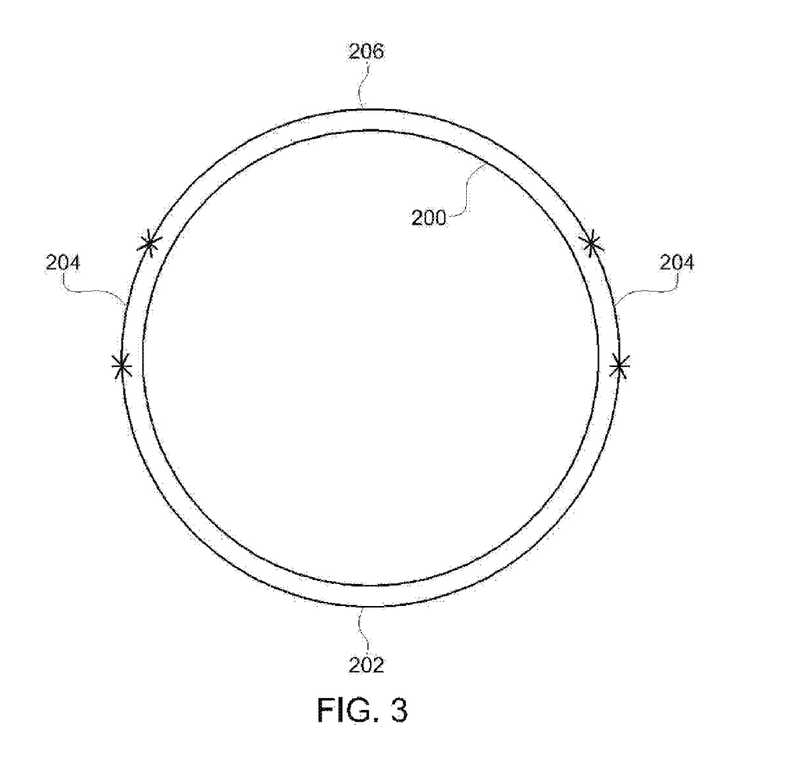
FIG. 3 is a visual representation showing radial locations where a set of projection data may be acquired in accordance with various embodiments.

For example, FIG. 3 is a visual representation showing radial locations where a set of projection data $y_{meas}$ may be acquired in accordance with various embodiments. As discussed above, the exemplary set of projection data $y_{meas}$ may be acquired at 102 when scanning at an angular range of approximately 180 degrees plus the fan angle plus the padding P. In the illustrated embodiment shown in FIG. 3, the projection data $y_{meas}$ is indicated by a line 200. As discussed above, the projection data $y_{meas}$ includes projection data acquired over 360 degrees. The projection data $y_{meas}$ includes subsets of projection data. For example, the projection data $y_{meas}$ includes a first subset of projection data 202 that represents the projection data acquired over 180 degrees ($\pi$). The projection data $y_{meas}$ also includes a second subset of projection data 204 that represents the projection data acquired over fan angle of 60 degrees ($\phi_{full}$). Thus, the subsets 202 and 204 represent projection data acquired during the short scan $(\pi+\phi_{full})$. The projection data $y_{meas}$ further includes a third subset of projection data 206 that represents the padding P. Thus, the subsets 202, 204, and 206 together form projection data projection data $y_{meas}$, which is also equivalent to $(\pi+\phi_{full}+P)$.

Referring to FIG. 2, the image 250 represents an exemplary image that may be reconstructed using the set of projection data $y_{meas}$ that may be acquired at 102. It should be realized that the image 250 is not displayed to the user. Rather, the image 250 merely provides a visual representation of the projection data $y_{meas}$ to better explain the various embodiments described herein.

Referring again to FIG. 1, at 104 the partial scan projection data, which in the exemplary embodiment, covers the angular range of $(\pi+\phi_{full})$, is extracted from the projection data $y_{meas}$ to form a partial scan projection dataset $y_{Partial}$ with corresponding reconstructed image $f_{PS}$. The partial scan projection dataset $y_{Partial}$ may cover any angular range within the projection data $y_{meas}$. For example, assuming that the projection data $y_{meas}$ extends 360 degrees, wherein the partial scan projection dataset $y_{Partial}$ extends a length of approximately 240 degrees, and an x-ray source is located at 0 degrees at the beginning of step 102, the partial scan projection dataset $y_{Partial}$ may extend from 0 degrees to 240 degrees. In the exemplary embodiment the partial scan is reconstructed to form an image with the short scan range ($f_{SS}$). Optionally, the partial scan projection dataset $y_{Partial}$ may extend from 10 degrees to 250 degrees, from 20 degrees to 260 degrees, etc.

At 106, a full scan projection dataset $y_{Full}$ is generated. The full scan projection dataset $y_{Full}$ may include all or just a subset of the projection information as $y_{meas}$. More specifically, the full scan projection dataset $y_{Full}$ cover the angular range of $(\pi + \phi_{full} + P)$. Optionally, the full scan projection dataset $y_{Full}$ may be acquired using, for example, data acquired over a range of $\pi$+the fan angle, data acquired from a multi-sector scan, data acquired from a multi-phase scan greater than 360 degrees, and/or using cine data. In the exemplary embodiment, the partial scan projection dataset $y_{Partial}$ encompasses less projection data than the full scan projection dataset $y_{FULL}$.

Referring to FIG. 2, the image 252 represents an exemplary image that may be reconstructed using the short scan projection dataset $f_{SS}$ generated at 104. Additionally, the image 254 represents an exemplary image that may be reconstructed using the full scan projection dataset $y_{FS}$ generated at 106. It should again be realized, that the image 252 and the image 254 are not displayed to the user. Rather, the image 252 and the image 254 merely provide a visual representation of the partial scan image dataset $f_{Partial}$ generated at 104 and the full scan image dataset $f_{Full}$ generated at 106, respectively, to better explain the various embodiments described herein.

For example, as shown in FIG. 2, the image 252 illustrates an exemplary vessel 253. However, the same vessel 253 shown in the image 254 appears to be two different vessels. More specifically, the motion in the image 254 represents the full scan projection dataset $F_{SS}$ which is acquired over a longer period of time than the short scan projection dataset $f_{SS}$. Thus, in various embodiments, the full scan image dataset $f_{Full}$ includes motion information that is not shown in the short scan projection dataset $f_{SS}$ which is acquired over a shorter period of time. Therefore, the motion information in the full scan projection dataset may result in blurring in the reconstructed image 254 that is not present in the image 252 which is reconstructed using the short scan projection dataset $f_{SS}$. Moreover, a wall 255 of the heart is also shown as moving in the image 254 as compared the heart in the image 252.

Referring again to FIG. 1, at 108 the full scan projection dataset $f_{Full}$ is subtracted from the short scan projection dataset $f_{SS}$ to generate a difference image dataset $f_D$. For example, and referring again to FIG. 2, the reconstructed image 252 is subtracted from the reconstructed image 254 to form the reconstructed image 256. As a result, the difference image 256 represents both the difference in noise between the image 252 and 254 and the difference in structural movement between the images 252 and 254.

Referring again to FIG. 1, at 110 a high-pass filter is applied to the difference image dataset $f_D$ to generate a high-pass filtered dataset $f_D^{HP}$. More specifically, in operation, the difference image dataset $f_D$ may include some low frequency differences caused by the difference in the effective weighting function. These very low frequencies do not contain quantum noise fluctuations as this noise is not correlated over large distances. Therefore, at 110 the high pass filter is applied to the difference image dataset $f_D$ to facilitate removing low frequency data. Referring again to FIG. 2, the difference image 256 is a high-pass filtered to generate a high-pass filtered image 258. In various embodiments, the high-pass filtered image 258 may include both noise and differences between the full and short scan projection datasets $f_{SS}$ and $f_{FS}$, respectively. The noise and differences may occur as a result of a temporal inconsistency between the full and short scan projection datasets $f_{SS}$ and $f_{FS}$, respectively.

Referring again to FIG. 1, at 112 an edge preserving filter is applied to the high-pass filtered dataset $f_D^{HP}$ to generate an inconsistency image dataset $f_I$ at 114. More specifically, the high-pass filtered dataset $f_D^{HP}$ may include both noise and temporal differences between the full and short scan projection datasets $f_{SS}$ and $f_{FS}$, respectively. Accordingly, the edge preserving filter facilitates generating the inconsistency image that includes very little quantum noise and the remaining content is attributable to any inconsistencies between the full and short scan projection datasets $f_{SS}$ and $f_{FS}$, respectively. The edge preserving filter may be, in various embodiments, a Total Variation (TV) minimization filter, a bilateral filter, or a non-local means filter, among others. In operation, the edge preserving filter is utilized to filter out noise in the high-pass filtered dataset $f_D^{HP}$ while preserving the edges of the structures in the image.

Referring again to FIG. 2, an edge preserving filter is applied to the high-pass filtered image 258 to generate an inconsistency image 260. In various embodiments, the inconsistency image 260 includes the various inconsistencies between the full and short scan projection datasets $f_{SS}$ and $f_{FS}$, respectively.

Referring again to FIG. 1, in order to isolate the noise difference between the full and short scan projection datasets $f_{SS}$ and $f_{FS}$, at 116, the inconsistency image dataset $f_I$ generated at 114 is subtracted from the high-pass filtered dataset $f_D^{HP}$ to generate a noise difference dataset $f^{ND}$. The noise difference dataset $f^{ND}$ therefore includes only the noise differences between the full and short scan projection datasets $f_{SS}$ and $f_{FS}$, respectively. An exemplary noise difference image 262 is shown in FIG. 2.

Referring again to FIG. 1, after the noise difference image 262 has been isolated from the temporal inconsistencies, by subtracting the noise difference image 262 from the inconsistency image 260, at 118, the noise difference dataset $f^{ND}$ is then subtracted from the short scan projection datasets $f_{SS}$ to generate a final image dataset $G_{final}$. The final image dataset $f_{final}$ may then be utilized to reconstruct a final image 264 of the object as shown in FIG. 2. More specifically, the image 262 illustrates the improvement to the image 250 after a single iteration of the various methods described herein are performed.

Figure 4:
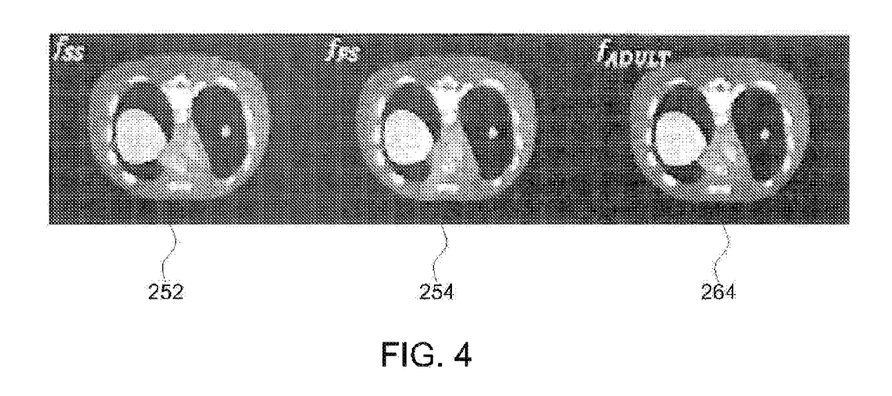
FIG. 4 is plurality of images that may be formed in accordance with various embodiments.

FIG. 4 illustrates a side-by-side comparison of the image 252 that may be reconstructed using the short scan projection datasets $f_{SS}$, the image 254 that may reconstructed using the full scan projection datasets $f_{FS}$, and the image 264 that is the final image that is reconstructed and displayed to the user. Accordingly, FIG. 4 illustrates the various noise compensation results that occur based on the various methods described herein.

Figure 5:
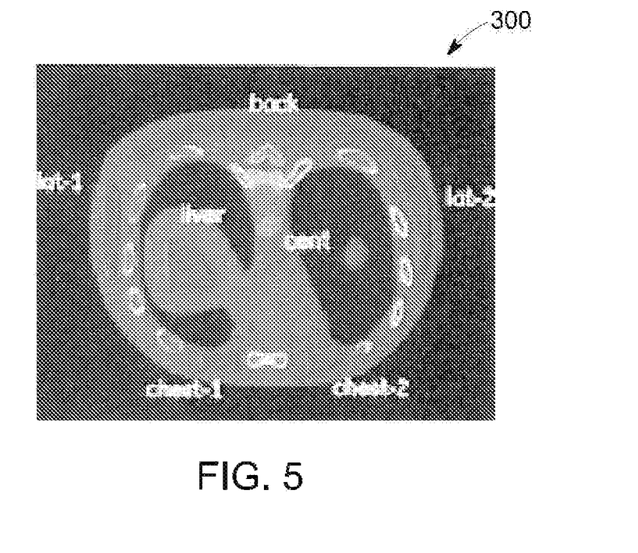
FIG. 5 is an exemplary image used to explain various embodiments described herein.

FIG. 5 is an exemplary image 300 that is utilized to demonstrate the noise reduction methods described herein. The image 300 is an axial image of an exemplary patient. Moreover, Table 1 shown below illustrates noise reductions that may occur using the various methods described herein. The first column in Table 1 refers to a specific region of interest (ROI) shown in the image 300 of FIG. 5. The second column shows the standard deviation ($\sigma$) in Hounsfield units (HU) at various locations in the image 252 which is generated using the short scan projection datasets $f_{SS}$. The third column shows the standard deviation ($\sigma$) in Hounsfield units (HU) at various locations in the image 254 which is generated using the full scan projection datasets $f_{FS}$. Finally, the fourth column shows the standard deviation ($\sigma$) in Hounsfield units (HU) at various locations in the final reconstructed image 264.

TABLE 1

| ROI | $\sigma_{fss}$ (HU) | $\sigma_{Fss}$ (HU) | $\sigma_{final}$ (HU) |
|---|---|---|---|
| center | 21.4 | 15.4 | 16.3 |
| chest-i | 16.1 | 11.8 | 11.5 |
| chest-2 | 17.2 | 12.1 | 12.8 |
| lat-i | 16.3 | 13.0 | 13.1 |
| lat-2 | 13.4 | 11.7 | 11.4 |
| back | 14.6 | 12.5 | 12.4 |
| liver | 23.6 | 17.1 | 18.3 |
| Mean | 17.4 | 13.3 | 13.6 |

As shown in Table 1, the standard deviation between the full scan data and the final reconstructed image are similar, therefore, in the areas shown in FIG. 5, the noise is similar to the noise in the full scan without compromising the temporal resolution.

Various embodiments described herein provide a technique for decomposing an imaged object f(x, y, z, C) into multiple regions based on temporal behavior. For example, in a certain region in the image there may be no temporal dependence, e.g. the spine, while in other regions there may be significant temporal dependence, e.g. the coronary arteries. Once the object has been decomposed based on the temporal characteristics the regions with no temporal dependence may be reconstructed using more projection data and hence the quantum noise will be reduced in these regions. The methods may be applied to data collected from any source trajectory.

In operation, the methods may be used with dynamic imaging techniques with axial and helical trajectories. Moreover, the methods make optimal use of the noise properties of the acquired data without sacrificing the improved temporal resolution of the reduced scan range acquisitions. The methods, in various embodiments, are computationally efficient in that the image computations are of the same computational order as the standard filtered backprojection image reconstruction. The methods may be utilized for a variety of imaging procedures, for example, standard cardiac exams, cardiac function exams, and neuro/cardiac perfusion measurements where dynamic data is acquired and there is a change in contrast throughout the examination.

More specifically, in operation, the methods described herein distinguish regions of the image where motion is present and regions that are motion free. Moreover, various methods provide optimal usage of the acquired projection data and reduce the use of phase based beam current modulation (e.g. reduced dose outside of the short scan). Since the projection data for a full scan is utilized in the reconstruction algorithm it is less important to reduce the delivered dose for views farther from the central phase. Thus, focus can be placed on anatomy based beam current modulation which may provide further dose reduction. Additionally, in the case of a system which is tube power limited this method may be used to enable noise reduction in the stationary regions of the image by applying this technique to data which does not have any beam current modulation.

Figure 7:
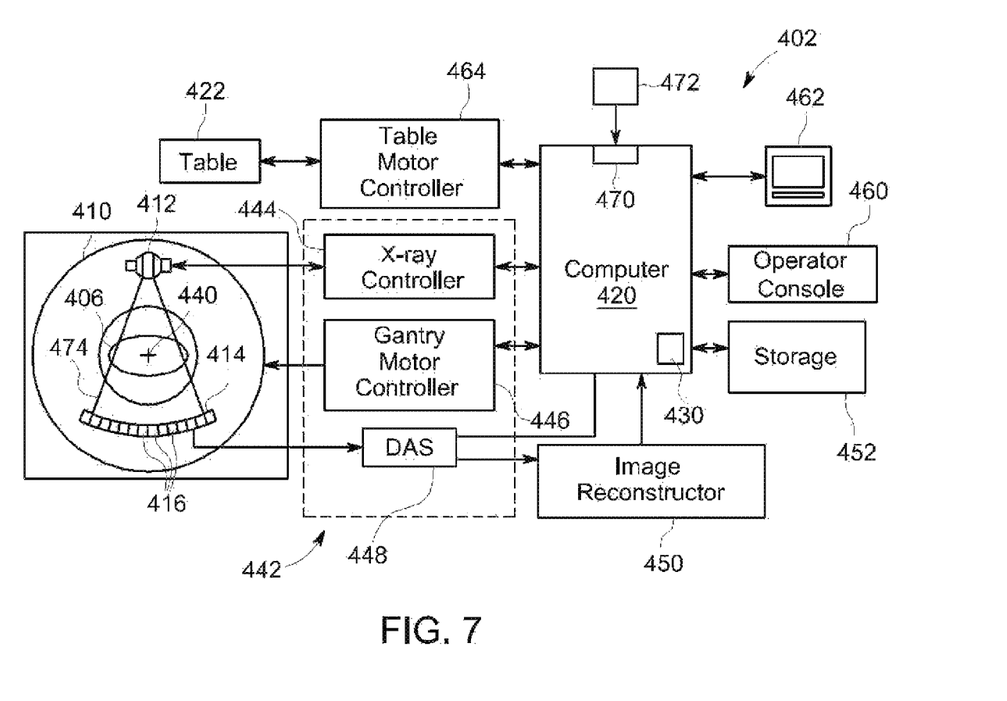
FIG. 7 is a block schematic diagram of the system illustrated in FIG. 6.

FIG. 6 is a pictorial view of an imaging system 400 that is formed in accordance with various embodiments. FIG. 7 is a block schematic diagram of a portion of the multi-modality imaging system 400 shown in FIG. 6. Although various embodiments are described in the context of an exemplary dual modality imaging system that includes a CT imaging system and a positron emission tomography (PET) imaging system, it should be understood that other imaging systems capable of performing the functions described herein are contemplated as being used.

The multi-modality imaging system 400 is illustrated, and includes a CT imaging system 402 and a PET imaging system 404. The imaging system 400 allows for multiple scans in different modalities to facilitate an increased diagnostic capability over single modality systems. In one embodiment, the exemplary multi-modality imaging system 400 is a CT/PET imaging system 400. Optionally, modalities other than CT and PET are employed with the imaging system 400. For example, the imaging system 400 may be a standalone CT imaging system, a standalone PET imaging system, a magnetic resonance imaging (MM) system, an ultrasound imaging system, an x-ray imaging system, and/or a single photon emission computed tomography (SPECT) imaging system, interventional C-Arm tomography, CT systems for a dedicated purpose such as extremity or breast scanning, and combinations thereof, among others.

The CT imaging system 402 includes a gantry 410 that has an x-ray source 412 that projects a beam of x-rays toward a detector array 414 on the opposite side of the gantry 410. The detector array 414 includes a plurality of detector elements 416 that are arranged in rows and channels that together sense the projected x-rays that pass through an object, such as the subject 406. The imaging system 400 also includes a computer 420 that receives the projection data from the detector array 414 and processes the projection data to reconstruct an image of the subject 406. In operation, operator supplied commands and parameters are used by the computer 420 to provide control signals and information to reposition a motorized table 422. More specifically, the motorized table 422 is utilized to move the subject 406 into and out of the gantry 410. Particularly, the table 422 moves at least a portion of the subject 406 through a gantry opening 424 that extends through the gantry 410.

The imaging system 400 also includes the module 430 that is configured to implement various noise compensation methods described herein. For example, the module 430 may be configured to reduce noise related artifacts in a medical image by correcting for a change in the noise between a fill scan set of projection data and a short scan set of projection data. The module 430 may be implemented as a piece of hardware that is installed in the computer 420. Optionally, the module 430 may be implemented as a set of instructions that are installed on the computer 420. The set of instructions may be stand alone programs, may be incorporated as subroutines in an operating system installed on the computer 420, may be functions in an installed software package on the computer 420, and the like. It should be understood that the various embodiments are not limited to the arrangements and instrumentality shown in the drawings.

As discussed above, the detector 414 includes a plurality of detector elements 416. Each detector element 416 produces an electrical signal, or output, that represents the intensity of an impinging x-ray beam and hence allows estimation of the attenuation of the beam as it passes through the subject 406. During a scan to acquire the x-ray projection data, the gantry 410 and the components mounted thereon rotate about a center of rotation 440. FIG. 7 shows only a single row of detector elements 416 (i.e., a detector row). However, the multislice detector array 414 includes a plurality of parallel detector rows of detector elements 416 such that projection data corresponding to a plurality of slices can be acquired simultaneously during a scan.

Rotation of the gantry 410 and the operation of the x-ray source 412 are governed by a control mechanism 442. The control mechanism 442 includes an x-ray controller 444 that provides power and timing signals to the x-ray source 412 and a gantry motor controller 446 that controls the rotational speed and position of the gantry 410. A data acquisition system (DAS) 448 in the control mechanism 442 samples analog data from detector elements 416 and converts the data to digital signals for subsequent processing. For example, the subsequent processing may include utilizing the module 430 to implement the various methods described herein. An image reconstructor 450 receives the sampled and digitized x-ray data from the DAS 448 and performs high-speed image reconstruction. The reconstructed images are input to the computer 420 that stores the image in a storage device 452. Optionally, the computer 420 may receive the sampled and digitized x-ray data from the DAS 448 and perform various methods described herein using the module 430. The computer 420 also receives commands and scanning parameters from an operator via a console 460 that has a keyboard. An associated visual display unit 462 allows the operator to observe the reconstructed image and other data from computer.

The operator supplied commands and parameters are used by the computer 420 to provide control signals and information to the DAS 448, the x-ray controller 444 and the gantry motor controller 446. In addition, the computer 420 operates a table motor controller 464 that controls the motorized table 422 to position the subject 406 in the gantry 410. Particularly, the table 422 moves at least a portion of the subject 406 through the gantry opening 424 as shown in FIG. 6.

Referring again to FIG. 7, in one embodiment, the computer 420 includes a device 470, for example, a floppy disk drive, CD-ROM drive, DVD drive, magnetic optical disk (MOD) device, or any other digital device including a network connecting device such as an Ethernet device for reading instructions and/or data from a non-transitory computer-readable medium 472, such as a floppy disk, a CD-ROM, a DVD or an other digital source such as a network or the Internet, as well as yet to be developed digital means. In another embodiment, the computer 420 executes instructions stored in firmware (not shown). The computer 420 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 412 and the detector array 414 are rotated with the gantry 410 within the imaging plane and around the subject 406 to be imaged such that the angle at which an x-ray beam 474 intersects the subject 406 constantly changes. A group of x-ray attenuation measurements, i.e., projection data, from the detector array 414 at one gantry angle is referred to as a "view". A "scan" of the subject 406 comprises a set of views made at different gantry angles, or view angles, during one revolution of the x-ray source 412 and the detector 414. In a CT scan, the projection data is processed to reconstruct an image that corresponds to a three-dimensional volume taken in the subject 406.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc., are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for reconstructing an image of an object, said method comprising:
acquiring a set of measured projection data;
reconstructing the measured projection data using a first algorithm to generate a first reconstructed image dataset, the first reconstructed image dataset reconstructed using a first temporal range of information from the measured projection data;
reconstructing the measured projection data using a second algorithm to generate a second reconstructed image dataset, the second algorithm being utilized to improve the temporal resolution of the second reconstructed image dataset, the second reconstructed image dataset using a second temporal range of information from the measured projection data that is less than the first temporal range, wherein the second temporal range defines a subset of the first temporal range; and
generating a final image dataset using both the first and second image datasets.

2. The method of claim 1, further comprising generating the final image based on a data consistency in a plurality of local regions, wherein the first reconstructed image dataset contributes more to a set of local regions having consistent data and the second reconstructed image dataset contributes more to a different set of local regions having inconsistent data.

3. The method of claim 1, further comprising subtracting the first reconstructed image dataset from the second reconstructed image dataset to generate a difference image dataset that includes temporal and noise differences between the first and second reconstructed image datasets.

4. The method of claim 3, further comprising:
filtering the difference image dataset using a high-pass filter; and
applying an edge preserving filter to the high-pass filtered difference image dataset to generate an inconsistency image dataset.

5. The method of claim 4, further comprising subtracting the inconsistency image dataset from the high-pass filtered difference image dataset to generate the noise difference image of the object.

6. The method of claim 3, further comprising:
applying an edge preserving filter to the difference image dataset to reduce a quantity of noise in the difference image dataset and to generate an inconsistency image dataset; and
subtracting the inconsistency image dataset from the second reconstructed image dataset to generate a noise difference image dataset.

7. The method of claim 6, further comprising subtracting the noise difference image dataset from the second reconstructed image dataset to generate the final image dataset.

8. The method of claim 6, wherein the edge preserving filter comprises at least one of a Total Variation (TV) minimization filter, a bilateral filter, or a non-local means filter.

9. The method of claim 1, wherein the first reconstructed image dataset is reconstructed from a first set of projection data having a first angular range and the second reconstructed image dataset is reconstructed from a second set of projection data having a second angular range that is less than the first angular range, wherein the first angular range comprises a desired phase, a fan angle, and padding, and wherein the second angular range comprises the desired phase and the fan angle but not the padding, wherein the second angular range defines a subset of the first angular range.

10. The method of claim 1, wherein the first and second reconstructed image datasets are reconstructed using the same set of projection data, the first reconstructed image dataset being reconstructed using different view weighting or different Fourier weighting than the second reconstructed image dataset.

11. An imaging system comprising:
an imaging scanner; and
a processor coupled to the imaging scanner, the processor configured to:
acquire a set of measured projection data;
reconstruct the measured projection data using a first algorithm to generate a first reconstructed image dataset, the first reconstructed image dataset reconstructed using a first temporal range of information from the measured projection data;
reconstruct the measured projection data using a second algorithm to generate a second reconstructed image dataset, the second algorithm being utilized to improve the temporal resolution of the second reconstructed image dataset, the second reconstructed image dataset using a second temporal range of information from the measured projection data that is less than the first temporal range, wherein the second temporal range defines a subset of the first temporal range; and
generate a final image dataset using both the first and second image datasets.

12. The imaging system of claim 11, wherein the processor is further configured to subtract the first reconstructed image dataset from the second reconstructed image dataset to generate a difference image dataset that includes temporal and noise differences between the first and second reconstructed image datasets.

13. The imaging system of claim 11, wherein the processor is further configured to:
filter the difference image dataset using a high-pass filter; and
apply an edge preserving filter to the high-pass filtered difference image dataset to generate an inconsistency image dataset.

14. The imaging system of claim 13, wherein the processor is further configured to subtract the inconsistency image dataset from the high-pass filtered difference image dataset to generate the noise difference image dataset.

15. The imaging system of claim 12, wherein the processor is further configured to:
apply an edge preserving filter to the difference image dataset to reduce a quantity of noise in the difference image dataset and to generate an inconsistency image dataset; and
subtract the inconsistency image dataset from the second reconstructed image dataset to generate a noise difference image dataset.

16. The imaging system of claim 15, wherein the processor is further configured to subtract the noise difference image dataset from the second reconstructed image dataset to generate the final image dataset.

17. The imaging system of claim 15, wherein edge preserving filter comprises at least one of a Total Variation (TV) minimization filter, a bilateral filter, or a non-local means filter.

18. The imaging system of claim 11, wherein the processor is further configured to:
reconstruct the first reconstructed image dataset using a first set of projection data having a first angular range; and reconstruct the second reconstructed image dataset using a second set of projection data having a second angular range that is less than the first angular range.

19. A non-transitory computer readable medium being programmed to instruct a computer to:
   acquire a set of measured projection data;
   reconstruct the measured projection data using a first algorithm to generate a first reconstructed image dataset, the first reconstructed image dataset reconstructed using a first temporal range of information from the measured projection data;
   reconstruct the measured projection data using a second algorithm to generate a second reconstructed image dataset, the second algorithm being utilized to improve the temporal resolution of the second reconstructed image dataset, the second reconstructed image dataset using a second temporal range of information from the measured projection data that is less than the first temporal range, wherein the second temporal range defines a subset of the first temporal range; and
   generate a final image dataset using both the first and second image datasets.

20. The non-transitory computer readable medium of claim 19, wherein the processor is further programmed to subtract the first reconstructed image dataset from the second reconstructed image dataset to generate a difference image dataset that includes temporal and noise differences between the first and second reconstructed image datasets.

21. The non-transitory computer readable medium of claim 20, wherein the processor is further programmed to:
   filter the difference image dataset using a high-pass filter; and
   apply an edge preserving filter to the high-pass filtered difference image dataset to generate an inconsistency image dataset.

* * * * *